United States Patent [19]
Klotz

[11] Patent Number: 5,725,563
[45] Date of Patent: Mar. 10, 1998

[54] ELECTRONIC DEVICE AND METHOD FOR ADRENERGICALLY STIMULATING THE SYMPATHETIC SYSTEM WITH RESPECT TO THE VENOUS MEDIA

[76] Inventor: Antoine Klotz, 1 Coeur de Maule, 78580 Maule, France

[21] Appl. No.: 537,794
[22] PCT Filed: Apr. 20, 1994
[86] PCT No.: PCT/FR94/00442
  § 371 Date: Oct. 23, 1995
  § 102(e) Date: Oct. 23, 1995
[87] PCT Pub. No.: WO94/23791
  PCT Pub. Date: Oct. 27, 1994

[30] Foreign Application Priority Data
  Apr. 21, 1993 [FR] France ............ 93 04687
[51] Int. Cl.$^6$ ............ A61N 1/36
[52] U.S. Cl. ............ 607/62; 128/734
[58] Field of Search ............ 607/62, 42–46, 607/5–8, 48, 50, 52, 58, 117, 118; 128/734; 127/734

[56] References Cited

U.S. PATENT DOCUMENTS 4,167,189  9/1979  Tachi et al. .

FOREIGN PATENT DOCUMENTS

| | | |
|---|---|---|
| 0 057 561 | 8/1982 | European Pat. Off. . |
| 1 148 312 | 7/1985 | European Pat. Off. . |
| 0 316 280 | 5/1989 | European Pat. Off. . |
| 0 425 673 | 5/1991 | European Pat. Off. . |
| 2 541 119 | 8/1984 | France . |
| WO 87/00760 | 2/1987 | WIPO . |
| WO 88/07392 | 10/1988 | WIPO . |

Primary Examiner—Marvin M. Lateef
Assistant Examiner—Kennedy J. Schaetzle
Attorney, Agent, or Firm—Young & Thompson

[57] ABSTRACT

A method and system for adrenergic stimulation of the sympathetic nervous system concerned with circulation of a patient in which electrical pulses are generated between at least two electrodes appropriately disposed on the patient. The impedance of all the cytoplasm between the electrodes is continuously measured, and the voltage of the pulses applied to the patient is continuously adapted to maintain the current at a constant value during a stimulation session regardless of variation of the cytoplasm.

22 Claims, 3 Drawing Sheets

ELECTRONIC DEVICE AND METHOD FOR ADRENERGICALLY STIMULATING THE SYMPATHETIC SYSTEM WITH RESPECT TO THE VENOUS MEDIA

The present invention concerns an electronic device for adrenergic stimulation of the sympathetic nervous system concerned with circulation.

Diseases relating to venous/lymphatic stagnation and to the vascular system are extremely common. Epidemiological studies show that thromboembolic disease is the third cause of death in the industrialized countries, for example, and that one in two persons over the age of 30 are suffering from incipient circulatory disorders. Furthermore, all athletes at a medium and high level will benefit from the use of physical methods to improve cellular trophism, to recover quickly after effort and to eliminate edema, hematoma and tendonitis.

Prevention and therapy are usually drugs-based, frequently accompanied by analyses and checks to verify their action. Clinical trials have shown the benefit and also the limitations of these methods, the use of which is very costly and has potential allergic or hemorragic side effects over and above their as yet limited effectiveness.

For this reasons researchers have attempted to develop physical treatment methods as more effective complements to or substitutes for the use of drugs.

Interesting results have been obtained from sequential pneumatic compression using boots to compress and decompress the lower limbs with a rhythm producing an improvement in flow. The use of such boots has given positive results. However, the equipment is complicated to use, is not sterile and its effectiveness is limited by the absence of deep effects.

A number of equipments for stimulating the "Polock" triceps surae are described in the literature but they cannot be used when the patient is awake.

The equipment described in German patent No 976 354 (Gratzel) refers to the stimulation of striated muscle by means of electrical pulses.

French patent No 2 493 437 (Baulande) concerns a method and equipment for stimulating contraction of striated muscles using unidirectional electrical pulses to activate the physiological calf muscle pump. This treatment is based on earlier therapeutic proposals of PROWS and KAKKAR.

However, the Baulande patent does not describe any means for monitoring the effectiveness of the treatment during administration or to protect the patient from hazardous stray electrical currents.

In European patent No 0137007 this applicant describes a device for stimulating the smooth muscles of the vascular tissue in which a high level of safety is provided by filters connected to the parts in contact with the body of the patient and to the power supply of the device. The current is regulated during treatment in accordance with information from sensors placed on the body of the patient (heat, rheological, resistive, myographic, Doppler, etc type sensors).

Clinical trials have shown the originality and the effectiveness of this equipment. However, it does not provide a flexible and reliable way of monitoring the effectiveness of the treatment during its application.

The sensors placed on the body of the patient, although they can indicate the general effectiveness of the treatment, do not enable accurate and instantaneous tracking of the exact evolution of the needs of the patient as the treatment proceeds.

Failing instantaneous monitoring of the effects of the treatment, the latter cannot be continuously adapted to the exact requirements of the patient. As a result the treatment time is often too short or too long and the parameters (in particular the voltage) characterizing the electric pulses travelling through the body of the patient do not entirely match the nature and the intensity of the pain that the patient is suffering.

The present invention aims to alleviate these drawbacks by proposing an electronic device for adrenergic stimulation of the sympathetic nervous system concerned with circulation, this device including means for generating electric pulses between at least two electrodes appropriately disposed on the body of the patient, the current, the voltage, the waveform and the frequency of the electric pulses being variable.

In accordance with the invention, the electronic device includes means for measuring the impedance between the electrodes.

The intracytological and extracytological cytoplasm can be regarded as a heterogeneous gel containing 85% to 90% by weight of water and protein. It has been observed that the disorders and diseases mentioned above cause local variation in the impedance of the cytoplasm that can be measured in terms of the frequency and energy parameters of the stimulus. Thus the presence of a hematoma or an edema can cause an impedance difference of approximately $250\Omega$ to $800\Omega$ and thrombosis can cause an impedance difference of $\pm 100\Omega$ to $400\Omega$.

Although the lower limbs of a fit athlete each have an impedance varying between $800\Omega$ and $1\,200\Omega$, the impedance increases to between $1\,200$ and $3\,000\Omega$ in the event of serious fatigue after effort or in the presence of cramps due to the presence of residues of muscular combustion and lactic acid causing an edema inhibiting the venous and lymphatic return functions.

Thus measuring the local impedance of the cytoplasm provides an indication of the magnitude, the nature and the exact location of the disorders and allows the selection of a treatment for the patient exactly matching their needs and their capacities.

To be more precise, the invention enables two-fold monitoring of the results of therapy. During treatment, monitoring the instantaneous evolution of the impedance measures the venous distensibility and compliance. The absolute variation of the impedance over the treatment as a whole indicates the venous tone. This two-fold monitoring of the impedance of the cytoplasm doubly optimizes the treatment received by the patient.

These pulses cause adrenergic stimulation of the sympathetic nervous system concerned with circulation, the main source of noradrenaline. Vasoconstriction is induced by activation of the post-synaptic alpha-adrenergic receivers. The effects also include acceleration of venous and lymphatic return and emulation of the parietal tissue responsible for the tonus of the tunica adventitia which controls venous distensibility, compliance and diameter.

One advantage of the invention is that the impedance measurement can be applied directly to all of the cytoplasm between the electrodes providing the treatment. This can be the total mass of the members or of a portion of the body of the patient, regardless of the volume of that portion, rather than only a section of the cytoplasm as is usual in rheographic impedance measurement, well-known in functional medical investigation. It is not necessary to use other electrodes for the impedance measurement, which makes the equipment easy to use. Moreover, the impedance is measured without looking for a particular impedance.

In an advantageous version of the invention the device includes means for varying the voltage of the pulses in accordance with the result of said impedance measurement.

For the operator, this simplifies the application of a treatment matched to the needs of the patient.

A preferred version of the device includes means for slaving the voltage of the pulses to the result of the instantaneous measurement of said impedance.

In this way the treatment is optimally adapted to the needs of the patient entirely automatically, relieving the operator of repetitive technical monitoring and intervention. If necessary, the treatment can therefore be administered to the patient by a person with no higher technical qualifications, for example a nursing auxiliary or the patient himself or herself.

In another preferred version of the invention the device comprises a reader for exchanging data with a removable data storage medium such as a memory card and the means for slaving the voltage of the pulses use data stored on said removable medium.

For example, each patient is given a removable medium of this kind containing medical data needed for their treatment. The use of this data by the device can enable automatic adjustment of the parameters of the treatment to be administered according to the needs of the patient and past treatment. Thus the use of the device is further automated, achieving even better adaptation to the needs of the patient and simplifying the task of the operator.

Other features and advantages of the invention will emerge from the following description of a preferred embodiment of the invention given by way of non-limiting example.

Figure 1:
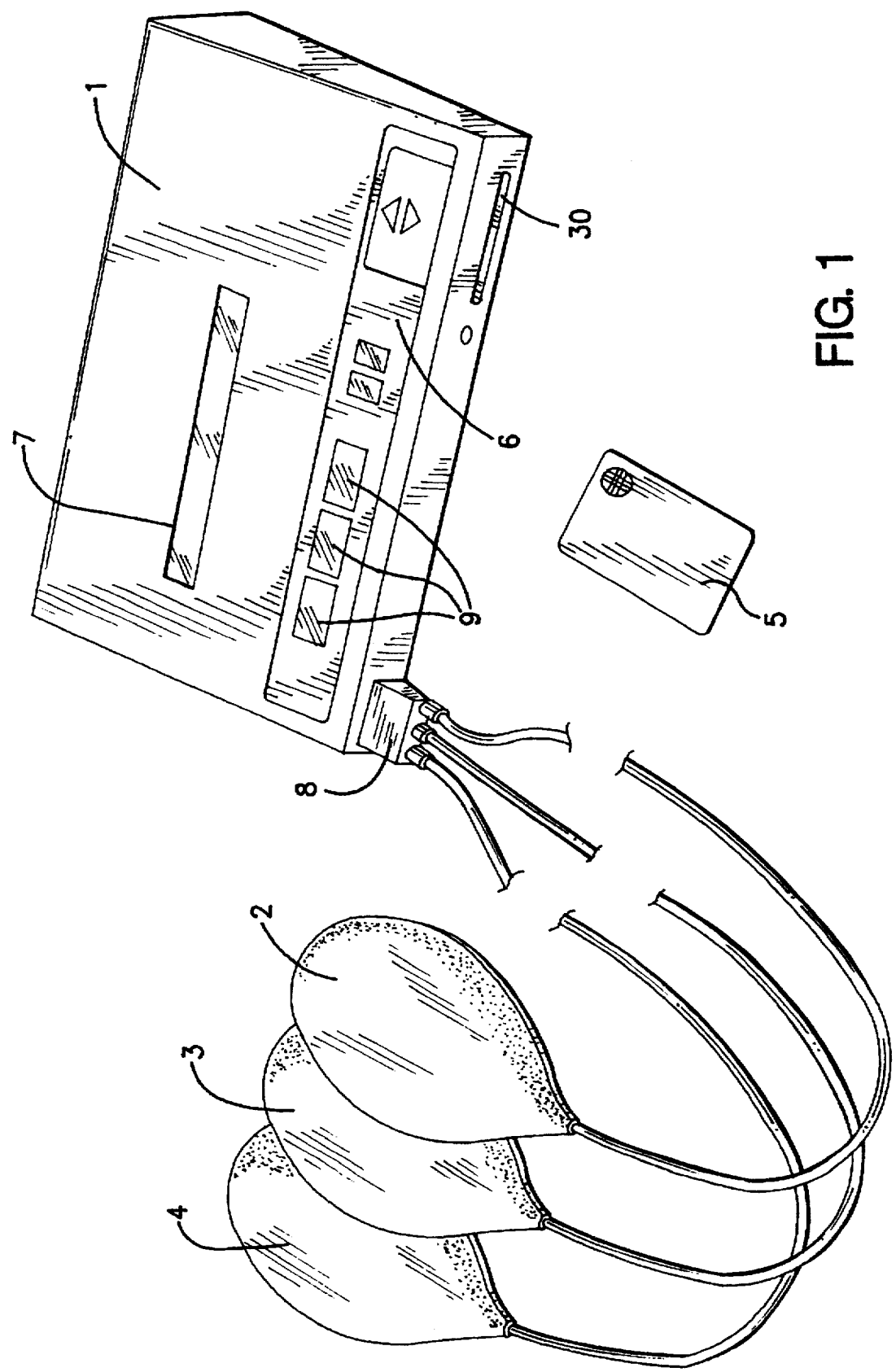
FIG. 1 is a perspective view of the device in accordance with the invention.

The device of the invention shown in FIG. 1 comprises a machine 1, three electrodes 2, 3 and 4 and a memory card 5 retained by and specific to each patient as well as an impedance measuring sensor.

The device is used to apply to the body of the patient a series of electric pulses described later of chosen current, voltage, waveform and frequency.

The machine 1 is a flat rectangular unit. It includes a control keypad with visual control keys relating to the various functions of the machine (insertion and withdrawal of the memory card, on/off switching, etc). It also includes three keys 9 constituting a touch-sensitive keypad. This can be used as a linear potentiometer, brushing the finger across the row of three keys varying the amplitude of the pulses to the required value. The machine 1 also has a liquid crystal display screen 7 for displaying commands and measurement results, for example, on two lines of characters. The cables from the three electrodes 2, 3, 4 are connected to the machine 1 via a plug 8.

Figure 2:
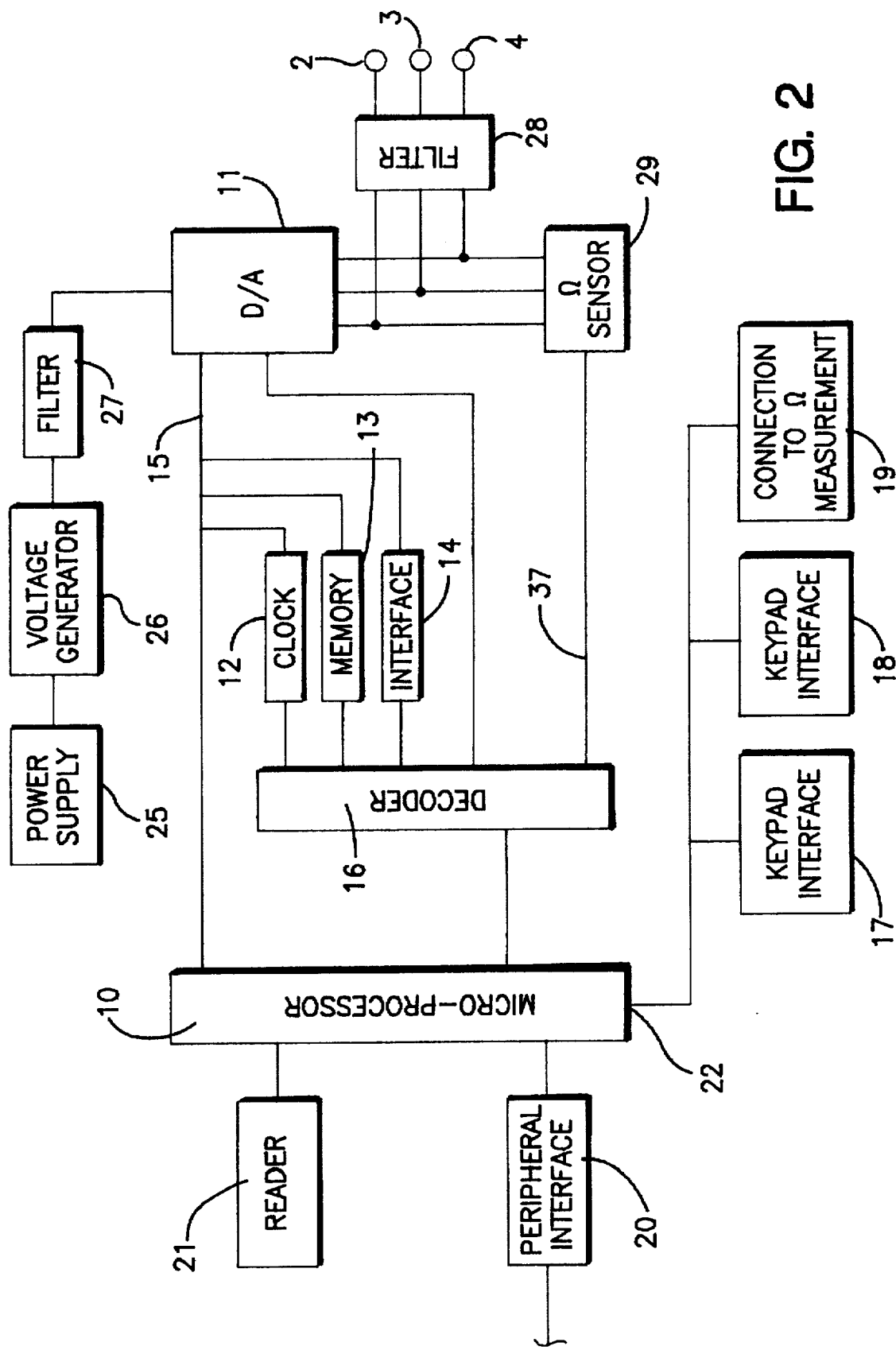
FIG. 2 is a diagram showing the main electronic components of the device and the general principle of their organization.

The electronic components of the machine 1 that generate and apply the pulses are conventional and widely known in the art. A large number of such components are described in document EP 0.137 007. The more important are described here, with reference to FIG. 2. The general organization of these electronic components is also evident to any electronics technician and is largely based on that described in the above document. FIG. 2 shows only the general principle of this organization.

The machine comprises firstly a microprocessor 10 controlling the generation and the application of the pulses in accordance with received data. The microprocessor 10 integrates a squarewave signal, this signal comprising the data needed to generate the pulses. The squarewave signal is passed to the digital-analog converter 11 which outputs the pulses passed into the body of the patient.

The microprocessor is conventionally associated with a clock 12, a random access memory (R) and a read-only memory (ROM), both memories being symbolically represented by the module 13, and an interface module 14 to which the display screen 7 is connected. The clock 12, the memories 13 and the module 14 are connected to the bus 15 connecting the microprocessor 10 to the digital-analog converter 11 and via a decoder 16 to the microprocessor 10. The microprocessor is also connected to the interface module 17 of the keypad 6, to the interface module 18 of the touch-sensitive keypad 9 and to the plug 19 connecting the impedance measuring sensor.

The microprocessor 10 is also connected to a connector 20 for connecting the machine to the usual data processing peripherals such as a printer, a modem, a computer or a Minitel terminal, for example via an infrared or shortwave radio link.

The microprocessor 10 is further connected to a reader 21 for a removable data storage medium 5. FIG. 1 shows the slot 30 through which the data medium is inserted into the reader. The medium may be a computer diskette but is preferably a conventional smart card or magnetic stripe card 5. For example, it can be a memory card, a microcontroller card, a PCMCIA card, etc. The card 5 can be retained by and specific to the patient, constituting their medical and epidemiological file. It contains all the data concerning the treatment of the patient (duration, number of sessions already carried out, pulse parameters, patient details, initial impedance value for the limbs of the patient, etc). If necessary the removable data storage medium could be read by the reader of a computer or other device.

The power supply of the digital-analog converter 11 includes a low-voltage power supply 25 that advantageously comprises an electric battery or group of electric cells. This power supply also supplies the other components of the machine (these power supply connections are not shown) and the machine as a whole is therefore self-contained and portable.

The power supply 25 is connected to a voltage generator 26 including an integral transformer (not shown) capable of increasing the low voltage output of the supply 25 to a voltage of 100 volts. The maximum current that can be output by this transformer is in all cases less than 3 milliamperes. Thus the pulse current is never hazardous to the patient.

The voltage generator 26 is connected to a filter 27 in turn connected to the converter 11. The function of the filter 27 is to keep out of the converter 11 accidental currents and voltages that could interfere with the treatment or be hazardous to the patient. The filter 27 can comprise an appropriate bandpass filter.

The converter 11 is connected to the three electrodes 2, 3 and 4 via another, similar filter 28. The role of this filter is to block entry via the electrodes 2, 3 and 4 of any unwanted exterior current likely to disrupt the operation of the device or the treatment of the patient. Such currents can be generated by radiological equipment, an electrical bistoury, etc.

The filter 28 includes a relay that remains open unless the machine has been programmed to treat the patient in complete safety.

The electrodes 2, 3 and 4 are preferably silicone resin films charged with conductive carbon. The graphite that they contain is arranged in a layered structure that facilitates the flow of electrons. The electrodes have a very low impedance and are highly conductive. The cable connecting each electrode to the machine 1 has one end buried in the mass of the electrode. The cables and the electrodes are made from a material that can be sterilized in an autoclave.

One feature of the present invention is the provision of means for measuring the impedance at the electrode terminals. In this example these means comprise an electronic component 29 such as the ANALOG DEVICES AD734AQ. Such means are not novel in themselves and are widely known in the electronics art. On the other hand, their use in a device such as that of the invention is novel and procures substantial advantages explained later.

The three electrodes are placed at different locations on the body of the patient, the electrode 3 serving as a reference electrode. With the patient supine, the electrode 2 is placed under the left calf, the electrode 4 under the right calf and the reference electrode 3 under the sacrum or on the pubis. An appropriate gel enhances the contact between the skin of the patient and the electrodes, in the manner well-known in itself.

The three electrodes 2, 3 and 4 are connected to the impedance measuring component 29 via the filter 28. This device measures the impedance between two appropriately chosen electrodes, reflecting the variation in the corresponding cytoplasm.

The impedance can be measured between the electrodes 2 and 4, for example. Nevertheless, it is advantageous to measure the impedance between the electrodes 2 and 3, on the one hand, and the electrodes 3 and 4, on the other hand. This differential measurement of the impedance provides an impedance measurement corresponding to each limb. To measure the impedance between two electrodes the component 29 is supplied with input data comprising the potential at each electrode and the current flowing through it.

The result of the impedance measurement is then fed to the microprocessor 10. There are two ways to achieve this: the first way amplifies the result in its analog form and feeds it direct to the analog port 22 of the microprocessor 10 (connection not shown). Using this method, the maximal relative error between the result calculated and the result transmitted varies between 2% and 4%. The second option is to convert the analog result into a digital result before it is amplified. After amplification, this result is passed to the microprocessor 10 via the decoder 16. The connection 37 for this option is shown in full line in FIG. 2. This method produces a relative error between 0.1% and 1%, depending on the quality of the converter used; this is quite sufficient.

The accuracy of the measurement is ensured by double calibration of the machine: the machines are initially calibrated identically by the manufacturer. Each machine then calibrates itself during use, for example each time that it is used, the microprocessor 10 being programmed to carry out internal calibration of the machine at regular intervals using an internal reference that is known in itself.

This double calibration means that measurements on the same patient from various identical devices in accordance with the invention are consistent for a period of up to two years from manufacture of the device. This means that it is not necessary to use the same device to administer and monitor the treatment of a given patient.

When the microprocessor 10 has acquired the result of the impedance measurement, it adapts the squarewave signal fed to the converter 11 accordingly so that the voltage of the pulses applied to the patient allows for the decrease in the measured impedance. This measurement and this adaptation can be carried out continuously to slave the voltage of the output pulses. The formula $E=U^2.t/R$ can be used to maintain constant energy, for example, where U is the voltage, R the impedance and t the duration of the pulses.

The pulses are applied between the electrodes 2 and 4 in the form of a repetitive stream of single pulses at a very low frequency, the pulses being identical and all positive or all negative, or alternatively in the form of streams of pulses that are highly advantageously alternately negative and positive. The pulses can also be applied in the form of an uninterrupted series of pulses.

During an individual treatment session, the pulses applied between the electrodes have a constant root mean square current below 350 microamperes, advantageously below 250 microamperes, with an energy content of less than 10 millijoules. A current of this magnitude cannot have any polarizing, electrifying or ionizing effect or otherwise affect any metal prosthesis, intra-uterine device, copper-based contraceptive or cardiac pacemaker.

The use of a constant current with the pulse amplitude varying as the impedance varies means that the treatment applied is comparable throughout the treatment regardless of variations in the cytoplasm during the treatment.

Figure 3:
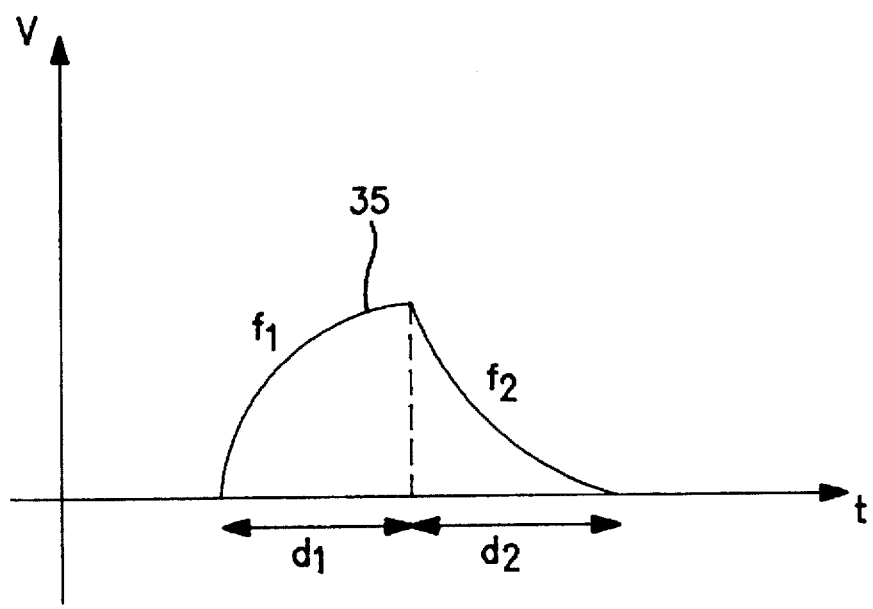
FIG. 3 shows one pulse waveform generated by the device.

FIG. 3 shows one example of the waveform 35 of the pulses. The abscissa axis and the ordinate axis respectively represent time and amplitude in volts V. The maximal rise time d1 of the pulses is 2 milliseconds. Their decay time d2 is equal to the rise time d1 and the shape of the decay curve f2 is the inverse of that of the rise curve f1. The rise curve is an exponential curve with an initial slope of 200 volts per millisecond. The frequency of the pulses is less than 2 Hz and preferably around 1.75 Hz.

The amplitude of the pulses varies between 0 V and 150 V or between −15 V and 0 V. The pulse voltage is slaved in the manner described above. Of course, the amplitude of the pulses can be selected manually, if necessary, for example using the keypad 6 and the touch-sensitive keypad 9.

The current and the voltage of the pulses can advantageously be chosen such that the energy of a pulse is between 0 mJ and 8 mJ. The polarity of the pulses can be positive, negative or alternately positive and negative, in various combinations. The duration of a session can vary from one second to several days, if necessary, and is typically 20 to 30 minutes or the time needed to carry out surgery. An advantageous range of frequencies is that between 0.75 Hz and 2.75 Hz.

The amplitude of the pulses can be slaved to the measured impedance and also, by virtue of use of the memory card 5, adapted to suit the individual patient. The card exchanges technical and medical data relating to the treatment and to the patient with the machine via the reader 21 and stores all parameters of the treatment as a whole as the latter proceeds. It enables automatic programming of the device as the treatment and the needs of the patient evolve. This makes the device very easy and very safe to use. The data on the card can also be used for economic, statistical and epidemiological studies and for maintenance or telemaintenance of the instrument. The device could be designed so that merely inserting the memory card into the machine 1 causes the latter to be reprogrammed automatically to generate pulses suitable for that particular patient.

The smart card advantageously has:

a system area: card number, month, year, department identification, serial number, etc;

a secret area for encrypting data exchanged with the microcontroller of the machine ensuring the safe treatment and preventing unauthorized access;

an interface area to the usual PCs: Power PC, Power MAC, MAC OS, OS2, DOS, UNIX, etc;

authorization levels: read only, transmit, write instrument only, writing of scheduling protocol by an external PC, authorized numbers of uses.

It further includes an identification area: treatment center, patient identity, type of illness, type of treatment, number of treatment sessions, duration, time and date, polarity, energy, sex, age, and a further 15 or so parameters that can characterize the type of patient treated, including: the impedance measurements for the patient at the start of the treatment, after 5 0, 15, 20 and 30 minutes, at the end of the treatment, total impedance, right, left.

A table of the measurements taken in the session and in previous sessions enables the practitioner to analyze the current condition of the patient, any progress over their previous condition, and their risk factors, in particular the risk of thrombosis.

This analysis of all the relevant data is visible on the screen of the machine for the person administering the treatment, can be interpreted directly by the machine and can be read by the doctor's or the hospital's external computer for collation into a database for epidemiological and statistical interpretation without any other data input by the person administering the treatment.

This analysis allows in particular diagnosis of the static or dynamic status of body fluids, proteins, fats, the mass of live, morbid and dead cells, the progress and rate of elimination, water or protein, of edema, hematoma or thrombus, the improvement in venous compliance.

If a risk factor threshold is breached: thrombus or edema, the instrument immediately alerts the person administering the treatment or the patient by visual and audible means, so that appropriate action can be taken without delay.

The smart card is written by the instrument the first time it is used on the patient and thereafter stores all events and measurements. It therefore becomes the ideal communication interface for long-term archive storage (ten years) and temporary storage (ABS) for the machine, that it then programs automatically, without the intervention of the personnel administering the treatment, for the doctor's PC, that it supplies with data as the basis for a diagnosis and enabling the provision of the treatment to be confirmed (time and date) and monitored, for epidemiological interpretation of data acquired accurately and economically, and for the security of the data, that it protects in accordance with applicable laws.

The facility to connect the device via the connector 20 to a printer, a modem, a computer or a Minitel terminal has many applications, for example in the remote provision of treatment or for the storage and archive storage of data.

The device of the invention can also include a movement sensor (not shown) such as those marketed by INTERLINK. The sensor is a flat disk approximately 20 millimeters in diameter. It is taped to the calf of the patient.

The electric pulses flowing in the body of the patient causes a physiological reaction of trembling of the surface of the members on which the pulses are acting. This trembling causes slight compression of the layer of carbon inside the sensor. The sensor has two internal electrodes connected to the machine and enabling a current to flow. The compression just referred to varies the resistance of the layer of carbon, and this is measured and transmitted to the microprocessor as an indication of the magnitude of the trembling.

For the treatment to be neither excessive nor insufficient, the trembling must lie between upper and lower thresholds that are known to the microprocessor 0 and that may depend on the individual patient. If either threshold is crossed, the microprocessor 10 modifies the squarewave signal supplied to the converter 11 in order to modify the voltage of the pulses to return the magnitude of the trembling to a point between the upper and lower thresholds.

The use of the movement sensor provides a further parameter, i.e. the magnitude of the trembling at the surface of the stimulated area, and this extra parameter is also used to control the voltage of the pulses applied to the patient, so that the treatment is that best suited to their needs.

The device can alleviate or cure many physiological disorders.

The advantages of electrical stimulation of circulation without using drugs include:

the freeing of fibrinolytic molecules, especially plasminogen and ATP, and direct diffusion (without passing via he synapses) to the striated muscle fibres, determining by the repetition of single pulses at a very low frequency regular compression of the veins followed by an ample period of relaxation, in the manner of a peristaltic pump, inducing by their physiological trembling the motor reflex of the pockets of the lymph system;

a progressive and durable training of the veins and the adjacent muscles and the restoration of an optimum tonus reducing the diameter of the veins and improving their compliance;

in the person treated using this device, acceleration of venous flow by a factor between 4 and 14;

total elimination of venous stagnation, known to be the major cause of thrombosis;

resorption of haemorrhoids and regressive varicose veins in women in childbirth;

elimination of pain, cramps and paresthesia due to venous-lymphatic syndrome;

acceleration of surface and deep venous return, microcirculation, lymph flow;

repolarization and recovery of the shape and the plasticity of erythrocytes and reduced viscosity of the blood;

improvement of the cardiac precharge, restoration of motor activity triggering hormonal metabolic and vital activity;

restoration of cellular trophism and elimination of cellular catabolism in bedridden patients;

elimination of aqueous edema, whether of banal origin or due to pregnancy, protein edema or hematoma, lysis and dispersal of aggregated leucocytes, erythrocytes, thrombi, lactic acid and uric acid crystals;

accelerated perfusion of oxygen and glucose.

This device is different from neuro-muscular and neurophysiological stimulamors which operate on the striated muscles of the skeleton through the intermediary of the synapses or motile platelets. Further advantages of the device stemming from this difference are that it cannot have any heating, polarizing or tetanizing effect, which means that it can be used on all categories of patients without contra-indications due to the presence of a metal prostheses, intra-uterine devices, copper-based contraceptives and cardiac pacemakers, for example.

An advantage of the invention is the ability to measure the variations between areas of the body caused by the applied stimulus to give an exact representation of the condition of the patient or to detect a risk factor, for example the presence of an obstacle to circulation such as a hematoma, an edema or a thrombus, by comparative or differential measurement of the mass of the two lower limbs. Similarly, measurement at specified intervals during the treatment gives an assessment and a qualitative measurement of the treatment and its effectiveness.

The timing and the duration of the sessions depend on the therapeutic and physiological needs of the patient. For a high-level athlete, after a major effort, three sessions each of 12 to 15 minutes during a period of one day return the impedance of the athlete's limbs to its initial value, representing full recovery of the athlete.

The safety of the patient is guaranteed by the use of a safe low-voltage power supply rated at less than 3 mA to generate the higher voltage.

This device is open to various modifications and improvements without departing from the scope of the invention, in particular with regard to the choice and the organization of the electronic components of the machine 1 and the characteristics of the pulses applied to the body of the patient.

I claim:

1. A method for adrenergic stimulation of the sympathetic nervous system concerned with circulation, said stimulation being made by electrical pulses (35) generated between at least two electrodes (2, 3, 4) appropriately disposed on the body of the patient, said method comprising the steps of:
   measuring the impedance of all the cytoplasm between the electrodes (2, 3, 4) providing the treatment; and
   adapting continuously the voltage of the pulses applied to the patient to maintain the current at a constant value during an individual stimulation session regardless of variation in the cytoplasm during the stimulation session.

2. The method according to claim 1, wherein the voltage of the electric pulses is slaved to the measurement of said impedance.

3. The method according to claim 1, wherein a root mean square value of the current is less than 350 microamperes.

4. The method according to claim 1, wherein the electrical pulses have a frequency less than 2 Hz.

5. An electronic device for implementing a method for adrenergic stimulation of the sympathetic nervous system concerned with circulation, the device comprising:
   at least two electrodes for being disposed on a body of a patient;
   means (10) for generating electrical pulses (35) between said at least two electrodes (2, 3, 4);
   means (7, 19) for measuring continuously the impedance of all the cytoplasm between the electrodes (2, 3, 4); and
   means for adapting continuously the voltage of the pulses applied to the patient to maintain the current at a constant value during a stimulation session regardless of variation in the cytoplasm during the stimulation session.

6. The device according to claim 5, wherein said means for adapting comprises:
   means (10) for adjusting the voltage of the pulses (35) as a function of measurement of said impedance.

7. The device according to claim 6, further comprising means (7, 19) for displaying a result of the measurement of said impedance.

8. The device according to claim 5, wherein said means for adapting comprises means (10, 36, 37) for slaving the voltage of the electric pulses (35) as a function of said impedance.

9. The device according to claim 5, further comprising a reader (21, 30) for exchanging data with a removable data storage medium (5).

10. The device according to claim 9, wherein said means for adapting is responsive to data stored on the removable storage medium (5) when read by said reader.

11. The device according to claim 5, further comprising a movement sensor for analyzing trembling of a surface of an area of the patient on which the pulses act.

12. The device according to claim 11, wherein said means for adapting is responsive to said movement sensor for analyzing trembling of the surface of an area of the patient on which the pulses act.

13. The device according to claim 5, further comprising first filter means (28) to which the electrodes (2, 3, 4) are connected, for preventing entry via the electrodes (2, 3, 4) of any external electric current likely to disrupt the operation of the device or the treatment of the patient.

14. The device according to claim 13, further comprising a power supply and second filter means (27) connected to said power supply for preventing the flow of an electric current other than a desired current between the electrodes (2, 3, 4).

15. The device according to claim 5, wherein the electric pulses (35) generated between the electrodes (2, 3, 4) have an effective current of less than 350 microamperes.

16. The device according to claim 5, wherein the frequency of the electric pulses (35) generated between the electrodes (2, 3, 4) is less than 2 Hz.

17. The device according to claim 5, comprising three said electrodes (2, 3, 4), one (3) of said three electrodes constituting a reference electrode for enabling comparative measurement of the respective impedances between said reference electrode and each of the other two said electrodes (2,4).

18. The device according to claim 5, wherein said electrodes (2, 3, 4) are made from silicone resin film impregnated with carbon.

19. The device according to claim 5, further comprising an autonomous power supply.

20. The device according to claim 5, further comprising interface means (20) for connecting data processing means.

21. An electronic device for adrenergic stimulation of the sympathetic nervous system concerned with circulation comprising:
   at least two electrodes for being disposed on a body of a patient;
   means for generating between said at least two electrodes electrical pulses which have selectively variable current, voltage, and frequency;
   means for measuring the impedance of the cytoplasm between said at least two electrodes;
   a movement sensor for analyzing trembling of a surface on which said at least two electrodes are disposed; and
   means for varying the voltage of said pulses in response to the measured impedance.

22. The device of claim 21, wherein said means for varying the voltage is further responsive to said movement sensor.

* * * * *